United States Patent
Urbanzyk

(10) Patent No.: US 9,222,861 B2
(45) Date of Patent: Dec. 29, 2015

(54) APPARATUS AND METHOD FOR MEASURING THE STRETCH OF A CHAIN WHICH CIRCULATES ENDLESSLY IN THE APPARATUS

(75) Inventor: Kai Urbanzyk, Weissensberg (DE)

(73) Assignee: Lindauer DORNIER Gesellschaft mbH, Lindau (DE)

( * ) Notice: Subject to any disclaimer, the term of this patent is extended or adjusted under 35 U.S.C. 154(b) by 0 days.

(21) Appl. No.: 14/111,861

(22) PCT Filed: Mar. 27, 2012

(86) PCT No.: PCT/EP2012/055382
§ 371 (c)(1),
(2), (4) Date: Oct. 15, 2013

(87) PCT Pub. No.: WO2012/156139
PCT Pub. Date: Nov. 22, 2012

(65) Prior Publication Data
US 2014/0102212 A1    Apr. 17, 2014

(51) Int. Cl.
*G01N 3/08* (2006.01)
*G01L 5/04* (2006.01)
(Continued)

(52) U.S. Cl.
CPC *G01N 3/08* (2013.01); *B65G 43/02* (2013.01); *G01B 21/06* (2013.01); *G01B 21/32* (2013.01)

(58) Field of Classification Search
CPC .......... B65G 43/02; G01N 3/08; G01B 21/32; G01B 21/06
USPC .......................................................... 73/828
See application file for complete search history.

(56) References Cited

U.S. PATENT DOCUMENTS 4,106,005 A * 8/1978 Asakawa ................. 198/810.02
5,291,131 A * 3/1994 Suzuki et al. ................. 324/206
(Continued)

FOREIGN PATENT DOCUMENTS

DE    199 02 759     8/1999
EP    1 464 919     10/2004
(Continued)

OTHER PUBLICATIONS

PCT Examiner Martinus Passier, International Search Report of the International Searching Authority for International Application PCT/EP2012/055382, mailed May 30, 2012, 2 pages, European Patent Office, HV Rijswijk, Netherlands.
(Continued)

*Primary Examiner* — Lisa Caputo
*Assistant Examiner* — Brandi N Hopkins
(74) *Attorney, Agent, or Firm* — W. F. Fasse

(57) ABSTRACT

An apparatus (2) with a chain (1) that is arranged endlessly circulateable in the apparatus (2) includes a measuring apparatus (3) for measuring the stretching or elongation of the chain (1), with a first signal pick-up (4) and with a second signal pick-up (5), which are arranged at a spacing distance (D) relative to one another, which extends in the running direction over several chain links (6) of the chain (1). A first element for signal generation (7) is arranged on a first chain link (6.1) in such a manner so that with a circulating chain (1) a signal is produced upon running past the first signal pick-up (4). Several further elements for signal generation (8) are arranged on a second chain link (6.2) in such a manner so that with a circulating chain (1) a further signal is generated with each one of these further elements (8) upon running past the second signal pick-up (5). During one circulation of the chain (1), the number (NS2) of signals at the second signal pick-up (5) is counted, which are produced before a first signal is produced at the first signal pick-up (4).

14 Claims, 4 Drawing Sheets

(51) Int. Cl.
  *G01M 13/02* (2006.01)
  *B65G 43/02* (2006.01)
  *G01B 21/06* (2006.01)
  *G01B 21/32* (2006.01)

(56) References Cited

U.S. PATENT DOCUMENTS

| 5,624,162 | A * | 4/1997 | Guse et al. ............ 299/1.6 |
| 6,291,991 | B1 | 9/2001 | Schnell |
| 6,851,546 | B2 * | 2/2005 | Lodge ............ 198/502.1 |
| 2004/0226805 | A1 | 11/2004 | Lodge |

FOREIGN PATENT DOCUMENTS

| EP | 1 873 088 | 1/2008 |
| GB | 2 406 844 | 4/2005 |
| JP | 59-078007 A | 5/1984 |
| JP | 05-081627 U | 11/1993 |
| JP | 07-268843 A | 10/1995 |
| JP | 2006-044853 A | 2/2006 |
| JP | 2010-190578 A | 9/2010 |

OTHER PUBLICATIONS

PCT Examiner Martinus Passier, English Translation of PCT Written Opinion of the International Searching Authority for International Application PCT/EP2012/055382, mailed May 30, 2012, 5 pages, International Bureau of WIPO, Geneva, Switzerland.

Japanese Office Action in Japanese Patent Application No. 2014-510704, mailed Nov. 28, 2014, 2 pages, with English translation, 2 pages.

* cited by examiner

APPARATUS AND METHOD FOR MEASURING THE STRETCH OF A CHAIN WHICH CIRCULATES ENDLESSLY IN THE APPARATUS

CROSS REFERENCE TO RELATED APPLICATIONS

This application is the 35 USC 371 National Stage of PCT International Application PCT/EP2012/055382 as filed on 27 Mar. 2012, and claims the 35 USC 119 priority of German Patent Application 10 2011 075 994.8 as filed on 17 May 2011.

FIELD OF THE INVENTION

The present invention relates to an apparatus and a method for measuring the stretch or elongation of a chain that circulates endlessly in the apparatus. Such apparatuses and methods are used, for example, in machines or plants for the transverse stretching of synthetic plastic films, so-called film tentering or stretching machines.

BACKGROUND INFORMATION

In film stretching machines in the prior art it is known to arrange chain links, which are connected together with one another to form a chain, in an endlessly circulateable manner in the film stretching machine. It is typical to use two parallel-running systems of chains that consist of chain links on which clamps for the film edge, so-called tenter clips, are arranged. The film is transported through the film stretching machine with the aid of the tenter clips. In that regard, the two chain systems are arranged so that their spacing distance transversely to the film transport direction gradually increases. Drive and deflection devices for each of the two chain systems are provided at the inlet and at the outlet of the machine. After the release of the film by the tenter clips at the outlet of the machine, the chain links with the tenter clips return back to the inlet of the machine outside of the film transport path.

The chain links run at a high speed and at an increased temperature. Therefore the connection joints between the individual chain links are subject to an undesired wear. Due to this wear, the spacing distance between the chain links becomes larger. A stretching or elongation of the respective chain arises, and upon exceeding certain magnitudes leads to operating disturbances and to faults in the film stretching process. In order to avoid these disturbances, it is necessary to carry out maintenance measures at the proper time. In order to determine this time point for the maintenance measures, measuring systems are known in the prior art, with which a stretch or elongation of the chain can be determined during the running operation of the chain.

Such a measuring apparatus is shown, for example, by the JP 2010 190578 A1. This measuring apparatus works with two sensors that probe and sense the contours of the chain links or the tenter clips. A geometric length for a certain number of chain links is determined from the time difference between two sensor signals and the current chain speed. The apparatus for monitoring a conveyor belt according to DE 199 02 759 A1 also operates with the evaluation of time differences between sensor signals. The JP 07-268843 A also discloses an apparatus for determining a stretch or elongation of a chain. Therein, however, an intensity difference of signals is evaluated instead of a detection time difference of two sensors. The intensity difference arises due to different positions of elements for signal generation that are applied or mounted on the chain. The EP 1 873 088 A1 describes an apparatus for determining wear-induced changes on the running surface of a belt. In that regard, magnetic signal generators that are embedded in the belt cause certain magnetic force progressions or patterns, which are detected and electronically evaluated by one or more sensors.

SUMMARY OF THE INVENTION

The object of the present invention is to provide an apparatus and a method for length measurement on a chain, which operates independently of the chain speed.

This object is achieved with an apparatus and a method according to the independent claims.

The apparatus includes a chain that is arranged to be endlessly circulateable in the apparatus. For measuring the stretch or elongation of the chain or the length difference that arises between a first and a second operating condition, a measuring apparatus is provided with a first signal pick-up or transducer and with a second signal pick-up or transducer, which are arranged at a spacing distance from one another, which extends in the running direction over several chain links of the chain. A first element for signal generation is arranged on a first chain link in such a manner so that a signal is generated upon running past the first signal pick-up with a circulating chain. This element for signal generation may, for example, be an element with which optical signals can be generated. For that it is sufficient if elements are present on the chain link, which interrupt or reflect a light beam when the chain link runs past an optical signal pick-up, for example a light beam barrier. Serving that purpose can be mechanical contours of the chain link or mechanical contours of the elements for grasping and clamping a film, the tenter clips that are mounted or applied on the chain links of the tenter clip chain in a film machine. If the signal pick-up is a light beam barrier, it converts the detected optical signals into electrical signals, which are then further supplied to the evaluating unit. However, it is also conceivable to mechanically operate an electrical switch, which serves as a signal pick-up, with the aid of mechanical contours of the chain link or the tenter clips upon running past. It is clear to the skilled worker in the field, that also other principles for signal generation and signal pick-up are possible, such as, for example, a metallic element for contact-less operation of a magnetic or induction switch or piezoelectric or capacitive signal generation and signal pick-up principles.

The measuring apparatus comprises a second element for the signal generation, which is arranged on a second chain link in such a manner so that with a circulating chain, upon running past at a second signal pick-up a second signal can be generated. The possible embodiments of elements for signal generation and for signal pick-up correspond to those that were described for the first chain link. According to the invention, several further elements for signal generation are arranged on the second chain link in such a manner so that with each one of these further elements, with a circulating chain, upon running past at a second signal pick-up a further signal can be generated.

In carrying out the inventive method, within one circulation of the chain, the number of signals is counted at the second signal pick-up, which signals are generated before a first signal is generated at the first signal pick-up. Upon a stretching or elongation of the chain, the number of these signals increases. An evaluating unit is present on the inventive measuring apparatus, with which evaluating unit this number of signals at the second signal pick-up is countable.

However, with a slow running of the chain, a counting of the number of signals at the second signal pick-up by the operator would also be conceivable.

For carrying out the inventive method it is advantageous if the spacing distance of the two signal pick-ups is dimensioned such that in a first unstretched operating condition of the chain, within one circulation of the chain, a first signal and a second signal are generated, before a further signal is generated at the second signal pick-up. In the ideal case, in the first unstretched operating condition, both signals are generated simultaneously. In this case the evaluating unit determines no signals at the second signal pick-up that are generated before a first signal is generated at the first signal pick-up within one circulation of the chain. This is dependent on the precision of the position of the signal pick-ups and on the tolerances of the involved chain links.

Therefore it is advantageous to make the spacing distance of the two signal pick-ups adjustable in such a manner so that it corresponds to the spacing distance between the first and second element for signal generation in a first unstretched operating condition of the chain. The spacing distance between the first and the second element for signal generation increases due to the stretching or elongation of the chain. This is due to the fact that these two elements are arranged or mounted on different chain links and that the spacing distance thereof increases due to wear in the joints or connection elements between the chain links. That is to say, in a second stretched operating condition of the chain, the spacing distance between the first and second elements for signal generation is larger than in the first unstretched operating condition. As soon as the spacing distance increase or elongation of the chain due to the wear is greater than the spacing distance between the second and the further elements for signal generation, which are arranged on the same chain link, within one circulation of the chain one of these further elements on the second signal pick-up will generate a further signal before a signal is generated at the first signal pick-up by the first element for signal generation.

If large length differences of the chain are to be expected, it can be advantageous to arrange further elements for signal generation on further chain links in such a manner so that with a circulating chain a further signal is generateable with each one of these further elements upon running past at the second signal pick-up. In this case the precision of the measurement is influenced additionally by the current spacing distance between the individual chain links equipped with elements for the signal generation. The chain link spacing distance of these measuring chain links can, however, be taken into account from the beginning in the evaluation of the signals, for example by input into the evaluating unit. In that regard, the change of this chain link spacing distance of the measuring chain links due to wear during the operation of the chain is negligible relative to the total stretch or elongation of a chain having several hundred chain links. Thus, also in this case the result of the measurement of the stretch or elongation is sufficiently exact.

In order to provide the operator the information about the current condition of the chain, a further embodiment of the apparatus is characterized in that a geometric length is calculateable from the signals by means of the evaluating unit and is displayable or indicateable to the operator. An embodiment of the inventive method provides that this calculation is carried out using the number of those signals at the second signal pick-up which are generated before the signal at the first signal pick-up. It is also conceivable, however, that merely the number of the signals is indicated or displayed, which are generated at the second signal pick-up within one circulation of the chain, before a first signal is generated at the first signal pick-up. The more signals are counted, the greater is the stretching or elongation of the chain, and the operator can carry out the maintenance of the chain upon exceeding a prescribed number of signals.

The arrangement and the dimensions of the elements for signal generation are used for the abovementioned calculation of a geometric length or the stretching or elongation of the chain. A calculation example shall clarify this: assuming that there are ten elements for signal generation arranged at a spacing distance of $A=5$ mm on the second chain link or on a tenter clip, and these elements are $B=5$ mm wide. If now the evaluating unit determines, for example, that within one circulation of the chain, $NS2=5$ signals are generated at the second signal pick-up before a first signal is generated at the first signal pick-up, then a geometric length is calculated according to the equation $DL=(NS2-1)\times(A+B)$. In the present example the result $DL=40$ mm arises. That is the stretching or elongation of the chain in the partial range or area that extends along the chain in the current running direction in the apparatus from the first element for signal generation to the second element for signal generation. The value for this stretching or elongation DL determined in the current operating condition involves the length difference in the partial range or area of the measuring path relative to the previous operating condition of the chain in which within one circulation of the chain both signals are generated simultaneously at the first and second signal pick-up, or relative to the condition in which the first signal is generated at the first signal pick-up before more than one signal is generated at the second signal pick-up. The stretching or elongation DL of the chain determined in this manner in the partial range or area detected by the measurement can, if necessary, subsequently still be calculated over or converted to the total length of the chain. For this, the value DL is calculationally converted in the proportion or ratio between the number of the chain links that lie in the partial range and the total number of the chain links, to form a total stretch or elongation.

Signals that are generated at the first signal pick-up by the elements for signal generation of the second chain link during one circulation of the chain are ignored by the evaluating unit. Similarly, the signal that is generated at the second signal pick-up by the element for signal generation of the first chain link during one circulation of the chain is also ignored.

Such an apparatus can be used everywhere where the length change of an endlessly circulating chain is to be determined without consideration of the chain speed. The use in a film stretching machine is especially advantageous. If a maintenance or an exchange of the tenter clip chain is carried out at the proper time due to the measuring result, quality impairments or production losses will be avoided. It is also conceivable to use this measuring apparatus in order to provide the signals regarding the stretch or elongation of two parallel-running tenter clip chains to the drive units for these tenter clip chains in the film stretching machine. With the aid of these signals, the synchronous running of the two chains during the transport of a film can thereby be supported.

DETAILED DESCRIPTION OF EXAMPLE EMBODIMENTS OF THE INVENTION

Figure 1:
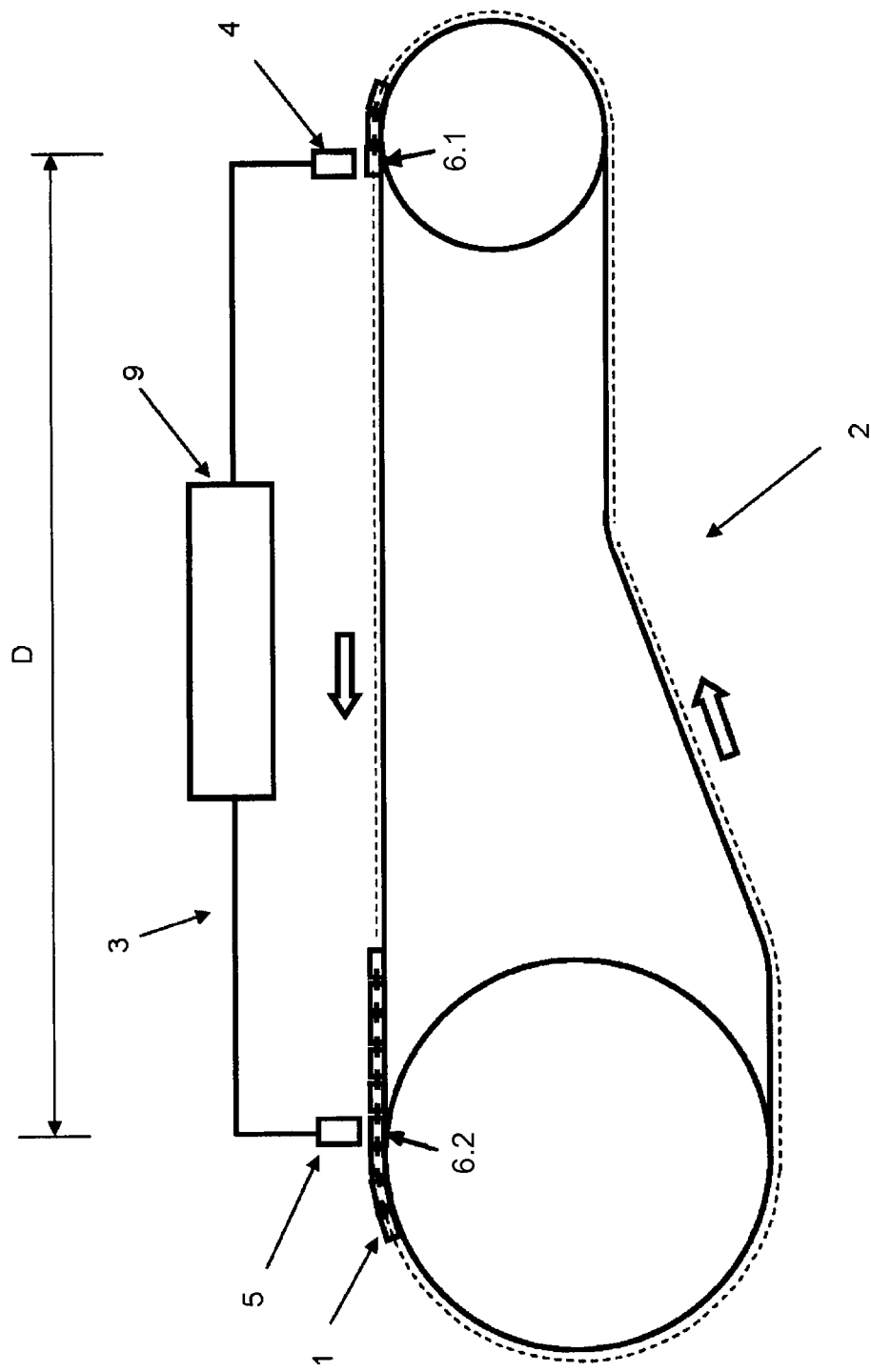
FIG. 1 schematic illustration of an embodiment of the inventive apparatus.

FIG. 1 shows an apparatus 2, which comprises elements for driving and deflecting a chain 1 that circulates endlessly in the apparatus 2. In the figures, the chain links are schematically illustrated only in the partial areas of the chain that are of interest here. The apparatus 2 according to FIG. 1 could, for example, be a component of a film stretching machine, in which however two of such apparatuses 2 would have to be arranged in a mirror symmetrical manner, so that a film can be transported between the two parallel-running chains 1. FIG. 1 shows the measuring apparatus 3 with the two signal pick-ups or transducers 4 and 5, which are arranged at a large spacing distance D from one another. In a film stretching machine this arrangement is best achieved in the area in which the tenter clip chain 1 runs back from one end to the other end of the machine outside of the film area. The signal pick-ups 4, 5 are electrically connected with an evaluating unit 9 belonging to the measuring apparatus 3. The signal pick-ups 4, 5 used in the measuring apparatus 3 of the present embodiment involve inductive proximity or approach sensors, which emit an electrical signal when a metallic object is moved past the sensor at a small distance. The securing of the sensors is carried out in a manner that enables an adjustment of the spacing distance D in the running direction of the chain 1.

Figure 2:
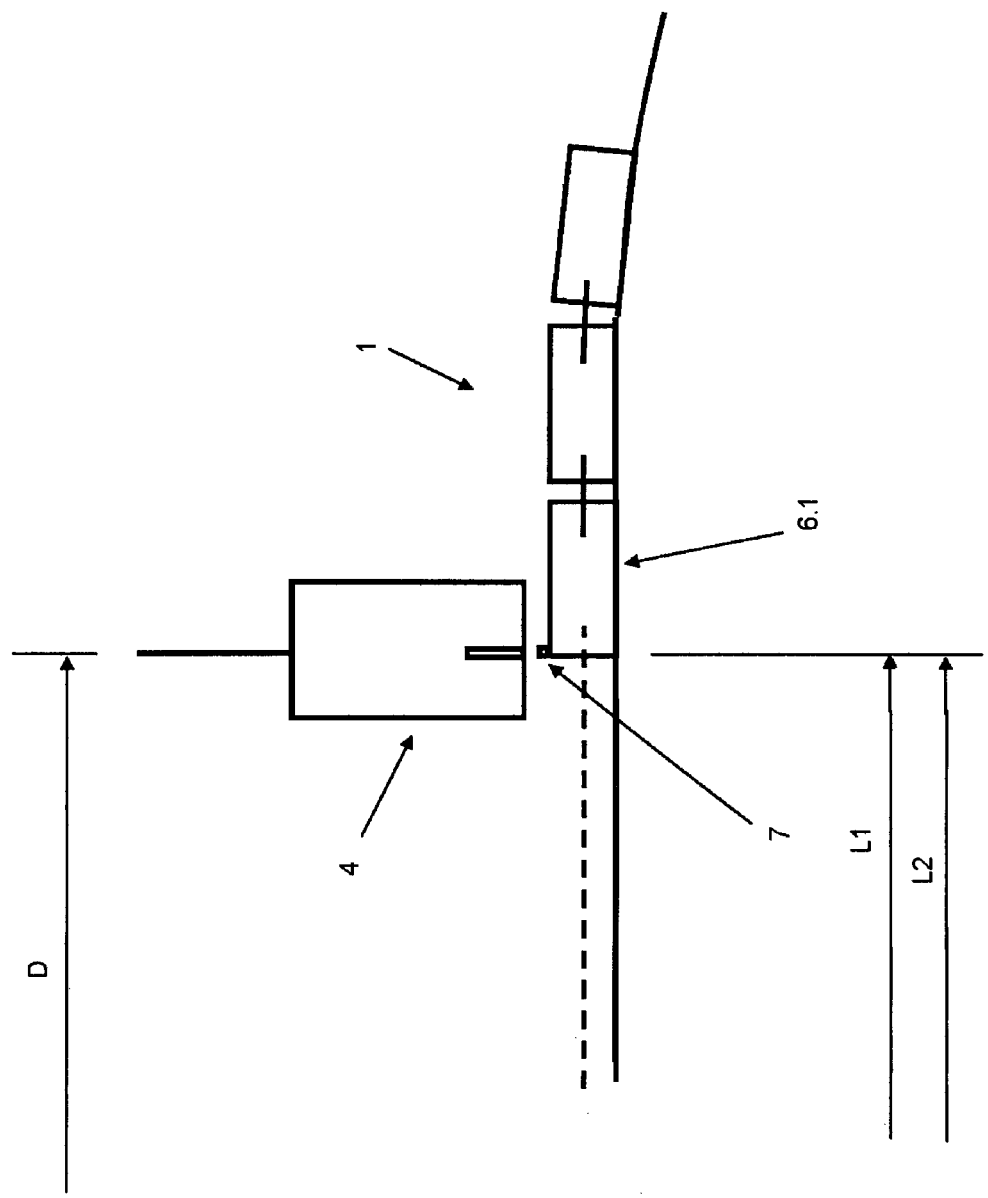
FIG. 2 enlarged view of the apparatus according to FIG. 1 in the area of the first signal pick-up.

FIG. 2 shows, on an enlarged scale, the area of the apparatus 2 in which the first signal pick-up 4, the inductive sensor, is arranged at a small spacing distance relative to the chain links 6. The first chain link 6.1 is equipped with a first element for signal generation 7. In the present example embodiment of the inventive apparatus 2, the elements for signal generation 7, 8 arranged on the chain links 6 consist of small metal blocks that are mounted on the side of the chain links 6 facing toward the signal pick-ups 4, 5. In a film stretching machine, the block-like signal generators 7 are mounted on a suitable or fitting surface of the tenter clips, which form chain links 6. The meaning of the spacing distances L1 and L2 is evident from the FIGS. 3 and 4.

Figure 3:
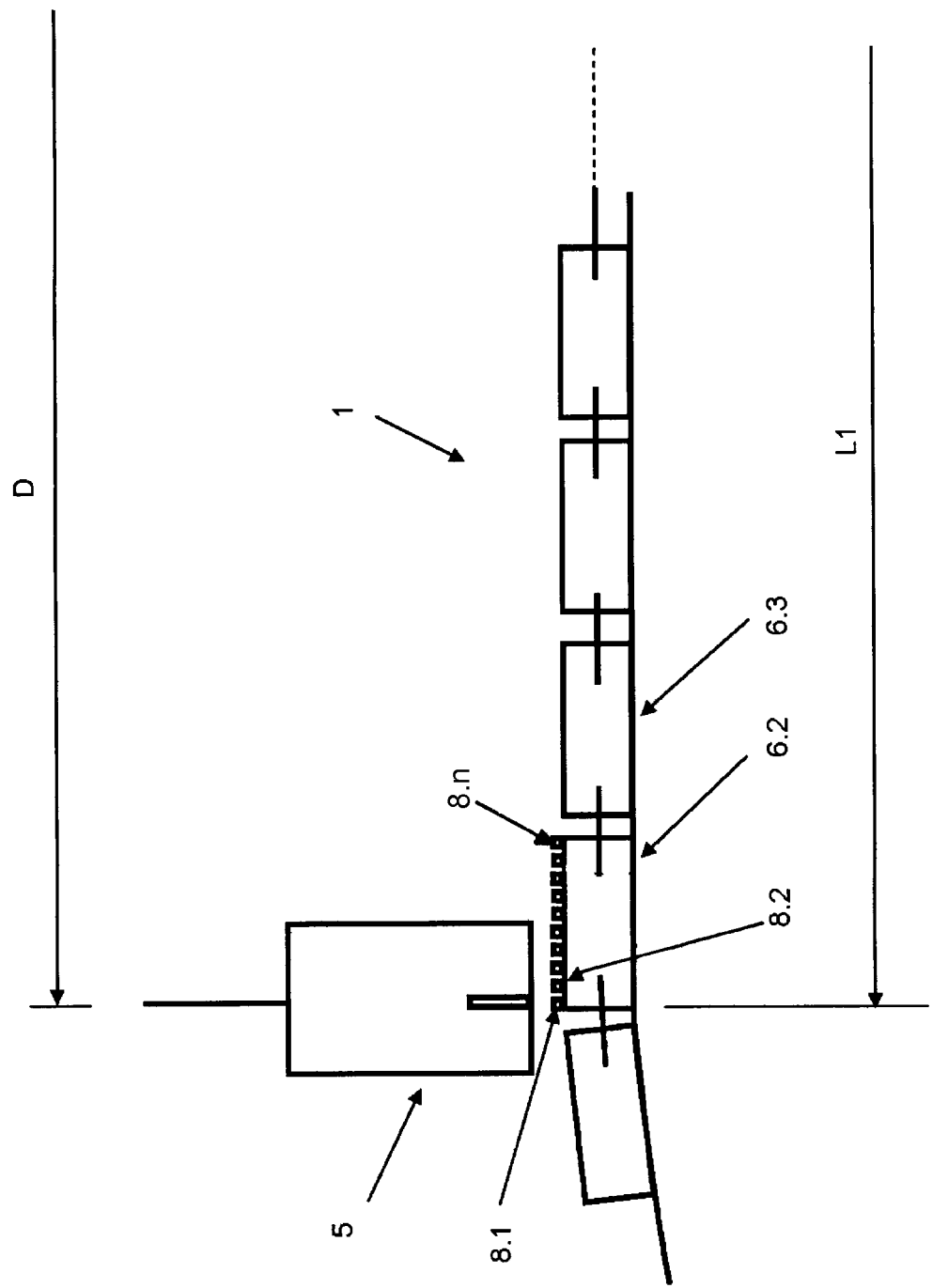
FIG. 3 enlarged view of the apparatus according to FIG. 1 in the area of the second signal pick-up for an unstretched chain.

FIG. 3 shows the apparatus 2 according to FIG. 1 in an enlarged partial view in a first operating condition of the chain 1. A second signal pick-up 5 is present, which is arranged at a spacing distance D from the first signal pick-up 4 in the measuring apparatus 3. Furthermore, a second element for signal generation 8.1, a block-like signal generator, is mounted on a second chain link 6.2. In this first operating condition, the spacing distance D is adjusted to the same dimension as the spacing distance L1 between the first element for signal generation 7 and the second element for signal generation 8.1 on the first chain link 6.1 and the second chain link 6.2 respectively. The first operating condition is preferably the unstretched condition of the chain 1 that is not yet worn. As needed, however, the operator can newly adjust the spacing distance D to the actual spacing distance L1 for every operating condition of the chain 1. According to the invention, the second chain link 6.2 comprises several further elements for signal generation 8.2 . . . 8.n. These are all mounted in such a manner so that when running past the second signal pick-up 5 an electrical signal is generated, which is supplied further to the evaluating unit 9. For determining larger amounts of stretch, the arrangement of additional elements for signal generation 8.m on a further chain link 6.3 is possible at any time, although not shown in the figures. Also conceivable is the exchange of entire chain links 6 without elements for signal generation 8 with such chain links that comprise several elements for signal generation 8.

Figure 4:
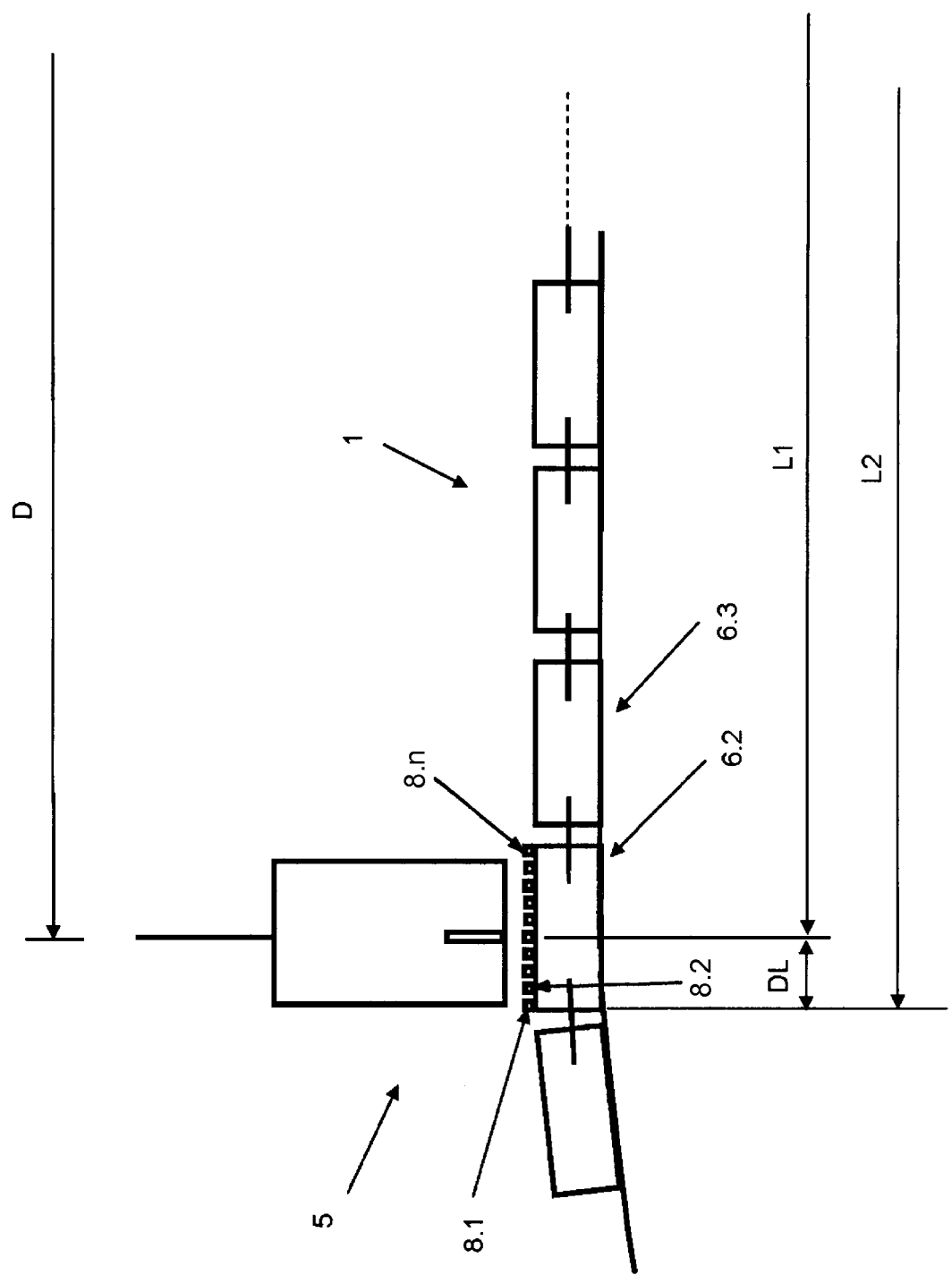
FIG. 4 enlarged view of the apparatus according to FIG. 3 in the area of the second signal pick-up with stretched chain.

FIG. 4 shows the apparatus 2 according to FIG. 3 in a second operating condition of the chain 1. This second operating condition is characterized by a stretching or elongation of the chain 1 by the amount DL relative to the first operating condition. Due to this stretching or elongation, the spacing distance between the first element for signal generation 7 on the first chain link 6.1 and the second element for signal generation 8.1 on the second chain link 6.2 becomes larger; the dimension L1 becomes the dimension L2.

During one circulation of the chain 1 in the apparatus 2 in the second operating condition, the following processes take place:

- the second element for signal generation 8.1 on the second chain link 6.2 produces a signal at the second signal pick-up 5;
- further elements for signal generation 8.2 . . . 8.n on the second chain link 6.2 produce further signals at the second signal pick-up 5;
- the first element for signal generation 7 on the first chain link 6.1 produces a signal at the first signal pick-up 4;
- the evaluating unit 9 counts the number of the signals at the second signal pick-up 5 which are produced there before the first signal is produced at the first signal pick-up 4;
- the stretching or elongation DL in the partial area of the measuring path distance is calculated from the number of the counted signals and from the geometrical arrangement of the block-like elements for signal generation 8 on the second chain link 6;
- a total stretching or elongation of the chain is calculated from the stretching or elongation DL in the partial area and from the ratio between the number of the chain links that lie in the partial area and the total number of the chain links;
- the total stretching or elongation is numerically displayed or indicated on a display or indicator unit (which is not shown) of the measuring apparatus 3;
- upon exceeding a certain total stretching or elongation in the running operation of the apparatus 2, an optical warning signal is emitted to the operator.

REFERENCE CHARACTER LIST 1 chain
2 apparatus, in which the chain circulates
3 measuring apparatus
4 first signal pick-up
5 second signal pick-up
6.1, 6.2, 6.3 chain links
7 first element for signal generation
8.1 second element for signal generation
8.2, 8.3, . . . 8.n, 8.m further elements for signal generation
9 evaluating unit
D spacing distance between signal pick-ups
L1 spacing distance between the first and the second element for signal generation in the first operating condition of the chain
L2 spacing distance between the first and the second element for signal generation in the second operating condition of the chain
DL difference between L2 and L1
NS2 number of signals at the sensor 2

The invention claimed is:

1. An apparatus
   with a chain, which is arranged endlessly circulateable in the apparatus, and
   with a measuring apparatus with a first signal pick-up and a second signal pick-up, which are arranged at a spacing distance relative to one another, which extends in a chain running direction over several chain links of the chain, and with a first element for signal generation mounted on a first chain link of the chain so that as the chain circulates, when the first element runs past the first signal pick-up, a first signal is producible at the first signal pick-up, and with a second element for signal generation mounted on a second chain link of the chain different from the first chain link, so that as the chain circulates, when the second element runs past the second signal pick-up, a second signal is producible at the second signal pick-up, characterized in that additionally at least third and fourth elements for signal generation are mounted on the second chain link so that as the chain circulates, when the at least third and fourth elements run past the second signal pick-up, at least a third signal and a fourth signal are respectively producible at the second signal pick-up, and further comprising an evaluating unit configured and adapted to count, during one circulation of the chain, a number of the signals produced at the second signal pick-up before the first signal is produced at the first signal pick-up, and wherein the evaluating unit is further configured and adapted to determine an amount of stretching of the chain from the number of the signals that has been counted.

2. The apparatus according to claim 1, characterized in that the spacing distance between the first and second signal pick-ups is adjustable so as to correspond to a spacing distance between the first and second elements for signal generation in a first unstretched operating condition of the chain.

3. The apparatus according to claim 2, characterized in that in a second stretched operating condition of the chain, the spacing distance between the first and second elements for signal generation is larger than the spacing distance between the first and second elements for signal generation in the first unstretched operating condition.

4. The apparatus according to claim 1, characterized in that additional elements for signal generation are mounted on an additional chain link of the chain so that as the chain circulates when each one of the additional elements runs past the second signal pick-up a respective additional signal is producible at the second signal pick-up.

5. The apparatus according to claim 1, characterized in that a geometric length can be calculated as the amount of stretching by the evaluating unit from the number of the signals, and can be displayed to an operator of the apparatus on a display device.

6. A film stretching machine including an apparatus according to claim 1, further comprising, on the chain links, devices for grasping and clamping a film that is to be stretched by the film stretching machine.

7. A method for measuring a stretching of a chain that circulates endlessly in an apparatus with a first signal pick-up and a second signal pick-up, which are arranged at a spacing distance relative to one another, which extends in a chain running direction over several chain links of the chain, wherein a first signal is produced at the first signal pick-up by a first element for signal generation that is mounted on a first chain link of the chain, and wherein a second signal is produced at the second signal pick-up by a second element for signal generation that is mounted on a second chain link of the chain, characterized in that during one circulation of the chain, at least third and fourth signals are respectively produced at the second signal pick-up by at least third and fourth elements for signal generation that are additionally mounted on the second chain link, and in that during one circulation of the chain a number of the signals that are produced at the second signal pick-up before the first signal is produced at the first signal pick-up is counted, and further comprising determining an amount of stretching of the chain from the number of the signals that has been counted.

8. The method according to claim 7, characterized in that the spacing distance between the first and second signal pick-ups is adjusted so as to correspond to the spacing distance between the first and second elements for signal generation in a first unstretched operating condition of the chain.

9. The method according to claim 7, characterized in that a geometric length is calculated as the amount of stretching by an evaluating unit from the number of the signals that has been counted, and the geometric length is supplied to a further component of the apparatus.

10. The method according to claim 7, characterized in that the apparatus is a component of a film stretching machine, further comprising, on the chain links, devices for grasping and clamping a film that is to be stretched by the film stretching machine.

11. The apparatus according to claim 1, wherein the evaluating unit is configured and adapted to determine the amount of stretching of the chain independent of and without consideration of a running speed of the chain.

12. The method according to claim 7, wherein the amount of stretching of the chain is determined independent of and without consideration of a running speed of the chain.

13. The apparatus according to claim 1, wherein the elements for signal generation are respective passive elements that are detectable by the signal pick-ups, and wherein the signal pick-ups are respective active sensors configured and arranged to detect the elements for signal generation proximately passing by the respective active sensors.

14. The method according to claim 7, wherein the elements for signal generation are respective passive elements that are detectable by the signal pick-ups, and wherein the signal pick-ups are respective active sensors that detect the elements for signal generation proximately passing by the respective active sensors.

* * * * *

UNITED STATES PATENT AND TRADEMARK OFFICE
CERTIFICATE OF CORRECTION

| | | |
|---|---|---|
| PATENT NO. | : 9,222,861 B2 | Page 1 of 1 |
| APPLICATION NO. | : 14/111861 | |
| DATED | : December 29, 2015 | |
| INVENTOR(S) | : Kai Urbanzyk | |

It is certified that error appears in the above-identified patent and that said Letters Patent is hereby corrected as shown below:

<u>On the Title page,</u>
   insert Item --(30)    Foreign Application Priority Data
          May 17, 2011   (DE) ............. 10 2011 075 994.8--.

Signed and Sealed this
Twelfth Day of July, 2016

Michelle K. Lee
*Director of the United States Patent and Trademark Office*